United States Patent [19]

Rapoport et al.

[11] Patent Number: 5,025,027
[45] Date of Patent: Jun. 18, 1991

[54] CYCLIC CARBAMATE ANALOGUES OF (+)-PILOCARPINE

[75] Inventors: Henry Rapoport, Berkeley, Calif.; Per Sauerberg, Valby, Denmark

[73] Assignee: Regents of the University of California, Berkeley, Calif.

[21] Appl. No.: 446,486

[22] Filed: Dec. 5, 1989

Related U.S. Application Data

[63] Continuation-in-part of Ser. No. 317,760, Mar. 2, 1989, abandoned.

[51] Int. Cl.$^5$ ..................... A61K 31/42; C07D 263/04
[52] U.S. Cl. ................................. 514/376; 548/229; 548/344; 548/342
[58] Field of Search ........................ 548/229; 514/376

[56] References Cited

U.S. PATENT DOCUMENTS 4,332,813 1/1982 Firestone ........................... 548/229

OTHER PUBLICATIONS

Gonzales et al., Tetrahedron Letters, vol. 30, No. 16, pp. 2145-2148 (May 8, 1989).
Sauerberg et al., Chem. Abstr., vol. 110, Entry 231941 (p) (Jun. 1989).
Sauerberg et al., Jour. Med. Chem., vol. 32 (No. 6), pp. 1322-1326 (1989).
H. Bundgaard et al., J. Med. Chem., 28, 1985, p. 979.
Aboul-Enein et al., Meth. and Find. Exptl. Clin. Pharmacol., 4, 1982, p. 321.
Parameswaran et al., J. Med. Chem., 30, 1987, p. 936.
Gonzalez et al., "Synthesis of (+)-Pilocarpine Analogs with a 2-Oxazolidone Structure", Tetrahedron Letters, vol. 30, No. 16, 1989, pp. 2145-2148.

Primary Examiner—Donald G. Daus
Attorney, Agent, or Firm—Majestic, Parsons, Siebert & Hsue

[57] ABSTRACT

Pilocarpine analogues are provided having the structure

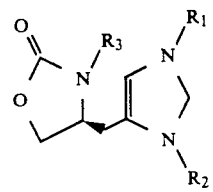

where one of $R_1$ or $R_2$ is an alkyl, such as methyl, ethyl, propyl, butyl, and so forth, and the corresponding secondary alkyl groups, an aralkyl, such as benzyl, phenylethyl, phenylpropyl, and the corresponding secondary aralkyl residues, or a cycloalkyl having less than about 12 carbon atoms. $R_3$ has at least two carbon atoms but less than about 9. These pilocarpine analogues have improved duration of biological activity with respect to pilocarpine. A particularly preferred compound is a muscarinic agonist equipotent with pilocarpine, where $R_2$ is methyl, and $R_3$ is ethyl.

6 Claims, 1 Drawing Sheet

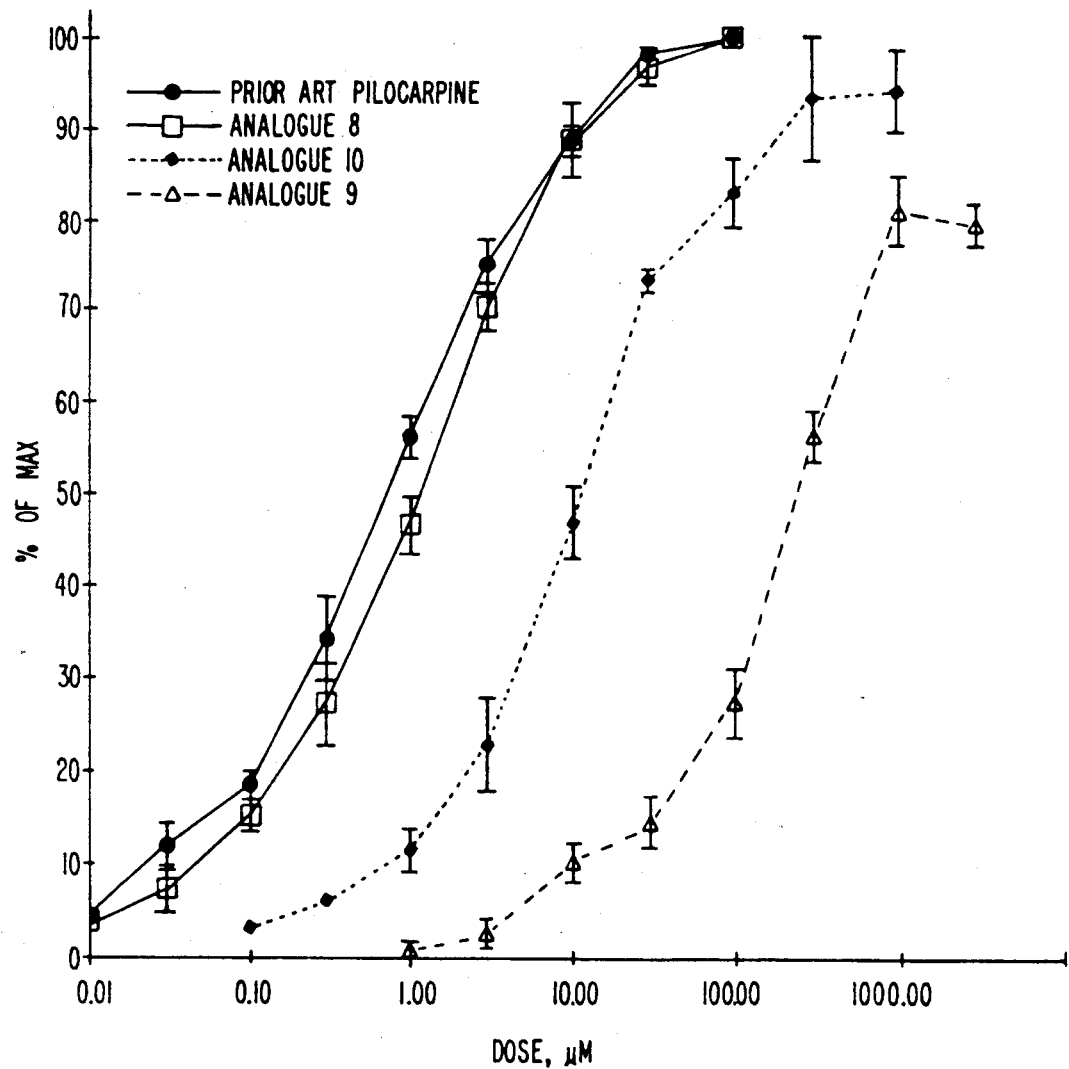

CYCLIC CARBAMATE ANALOGUES OF (+)-PILOCARPINE

This application is a continuation-in-part of S.N. 317,760, filed Mar. 2, 1989, now abandoned.

FIELD OF THE INVENTION

The present invention relates generally to analogues of (+)-Pilocarpine, and more particularly relates to cyclic carbamate analogues of (+)-Pilocarpine.

BACKGROUND OF THE INVENTION (+)-Pilocarpine, the most important imidazole alkaloid, has been the focus of much attention for many years because of its extensive pharmacological properties. These include diaphoretic effects, stimulation of the parasympathetic system, miotic action, and particularly applications in ophthalmology. Pilocarpine is currently the drug of choice for treatment of narrow and wide angle glaucoma because it decreases the intraocular pressure and can be administered for long periods without side effects. Pilocarpine, along with its epimer isopilocarpine, was first isolated in 1875 from various species of Pilocarpus plants belonging to the Rutaceae family. The structure of this alkaloid, proposed in 1900, was later confirmed in degradation studies, X-ray analysis, and several syntheses.

Pilocarpine is a cholinergic muscarinic agonist. Although widely employed as a topical miotic for controlling the elevated intraocular pressure associated with, qlaucoma, oilocaroine has the disadvantage in having a short duration of action. The duration of intraocular pressure lowering caused by Pilocarpine lasts only for about three hours, and consequently the frequency of administration can be 3-6 times a day.

SUMMARY OF THE INVENTION

It is an object of the present invention to provide pilocarpine analogues with improved duration of action with respect to pilocarpine.

In one aspect of the present invention biologically active pilocarpine analogues are provided having the structure

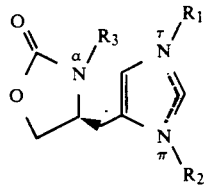

(where the dashed lines indicate the potential presence of a carbon-carbon double bond involving either the $N\tau$ or the $N\pi$), where one of $R_1$ and $R_2$ is a primary or secondary alkyl, a primary or secondary aralkyl, or a cycloalkyl, and where $R_3$ has between 2 to about 8 carbon atoms and is an alkyl, a cycloalkyl, an alkenyl or an alkynyl.

BRIEF DESCRIPTION OF THE DRAWING

FIG. 1 graphically illustrates biological activity of three analogues of the invention and of pilocarpine as contractions of guinea pig ileum when single doses of the respective compounds were administered.

DETAILED DESCRIPTION OF THE PREFERRED EMBODIMENTS (+)-Pilocarpine has a short duration of biological activity that is mainly due to hydrolytic cleavage of the lactone ring and/or epimerization to form isopilocarpine. Cleavage of the lactone ring results in the formation of pilocarpic acid. Both pilocarpic acid and isopilocarpine are essentially pharacologically inactive.

Analogues of the invention have the structure illustrated by Formula II, while pilocarpine is shown as Formula I.

FORMULA I
(Pilocarpine)

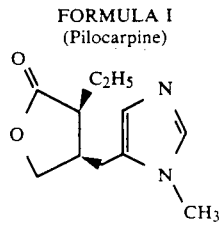

FORMULA II
(Inventive Analogues)

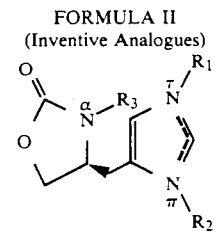

In the Formula II structure, one of the $R_1$ and $R_2$, substituent is a primary or a secondary alkyl, is a primary or secondary aralkyl, or is a cycloalkyl. Most preferred is where $R_2$, is methyl. However, when one of $R_1$ and $R_2$ is a primary or secondary alkyl other than methyl, then it may have less than about 12 carbon atoms, preferably less than about 8 carbon atoms, more preferably 2 to 6 carbon atoms. These primary or secondary groups can be branched or unbranched. When one of $R_1$ and $R_2$ is a primary or secondary aralkyl, then it preferably has less than 12 carbon atoms, more preferably between 7 to 9 carbons (including benzyl, phenylethyl, and phenyl propyl), and the phenyl ring can be unsubstituted or substituted. When one of $R_1$ and $R_2$ is a cycloalkyl, then it may have less than about 12 carbons atoms. Thus, $R_1$ or $R_2$ can be a wide variety of residues having less than about 12 carbon atoms. $R_3$ has at least two carbon atoms but less than about 9 carbon atoms, and is an alkyl, a cycloalkyl, an alkenyl or an alkynyl group. $R_3$ substituent groups with carbon atoms greater than or equal to about $C_2$ are useful to increase the liphophilicity of the analogues. As can be seen by comparing the Formula I pilocarpine structure with the Formula II inventive analogues, the lactone ring of pilocarpine has been replaced with a carbamate.

The Formula II analogues of the invention have a longer duration of biological activity in aqueous media than does pilocarpine. It is believed that the improved duration of action for compounds of the invention may be due in part because carbamates are more stable toward hydrolysis than lactones. Another reason for the improved duration of action may be due to the fact that a biological system such as a mammalian body does not have enzymes to hydrolyze carbamates. In any event, analogues of the invention display biological activity in the form of muscarinic effects. Indeed, a particularly preferred embodiment of the invention (wherein $R_2$ is methyl) is a muscarinic agonist equipotent with pilocarpine, yet with improved duration of action.

A method for preparing embodiments of the invention is generally set out in Reaction Scheme I where specific reference is made to preparation of three analogues of the invention.

tive 9 can be obtained at some stage of the sequence by debenzylation under standard conditions. Methylation of NH compound 9 gives a mixture of N$\pi$- and N$\tau$-methyl isomers 8 and 10 which are separable by chromatography. Assignment of the regiochemistry of 8 and 10 can then be done through NMR studies measuring the cross-ring coupling constants.

1-Benzyl-L-histidine 1 was synthesized from L-histi-

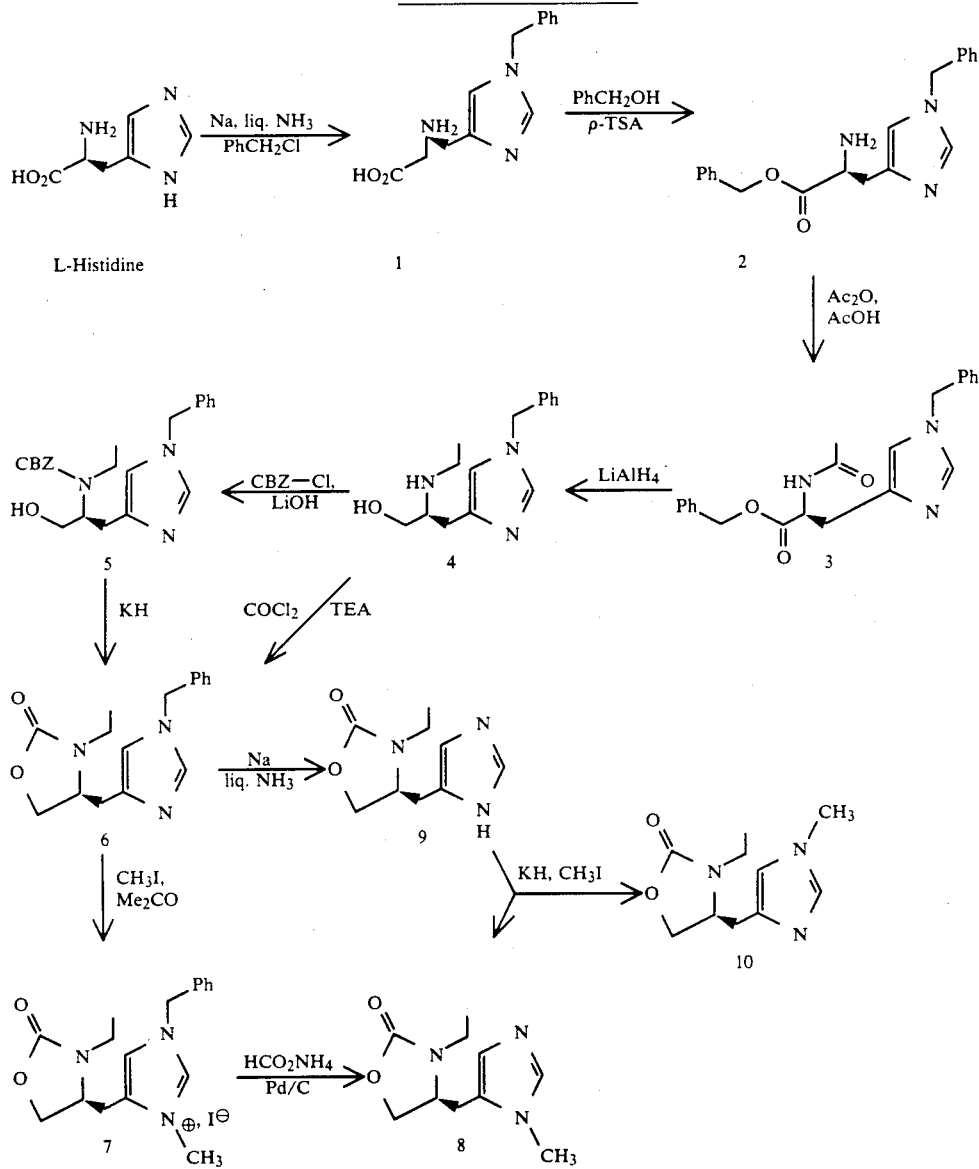

As is illustrated by Reaction Scheme I, the preparation of the inventive analogues may be achieved through use of $R_1I$ or $R_1Br$ or $R_2I$ or $R_2Br$. For some analogues, use of the bromide may be more convenient than the iodide. Where $R_3$ is an alkyl larger than ethyl, then one can substitute the corresponding higher anhydride or acid chloride for acetic anhydride in the conversion of 2 to 3.

In the Reaction Scheme I, histidine was chosen as the closely related chiral educt and benzyl was chosen as the imidazole ring protecting group because it would survive reduction of the ester and amide to the alcohol and secondary amine, respectively. Regardless of the position of the imidazole benzyl group, the NH derivadine, as described by du Vigneaud et al., *J.Biol.Chem.*, 117, pg. 27 (1937), and purified by fractional crystallization. The 1-benzyl-L-histidine benzyl ester 2 was the next compound of the sequence and was chosen because the additional benzyl group would increase the lipophilicity of the compounds, and because 2 has been reported to be more stable than the corresponding methyl ester. Acetylation of benzyl ester 2 to N-acetyl-1-benzyl-L-histidine benzyl ester 3 was carried out with acetic anhydride in glacial acetic acid. Nomenclature for histidine derivatives 1, 2, and 3 follows the *Chemical Abstracts* recommendation in which the histidine side chain is arbitrarily assigned to the 4-position of the imidazole ring. Although this rule may violate standard imidazole numbering, it has been adopted by *Chem. Abs.* only for the special case of histidines. For compounds 4 and after, we have applied standard imidazole nomenclature.

Reduction of 3 with $LiAlH_4$ gave 1-benzyl-4-(2,'-ethylamino-3,'-hydroxypropyl) imidazole 4. The histidinol 4 was either converted to the corresponding N-benzyloxycarbonyl derivative 5 with benzyl chloroformate and then cyclized to (S)-3-ethyl-4-(1,'-benzyl-4,'-imidazole)methyl-2-oxazolidinone 6, or 4 was cyclized directly to compound 6 with phosgene.

Proof of the regiochemistry of the imidazole benzyl group was provided by $^1H$ NMR studies at 500 MHz. The cross-ring coupling constant between the imidazole ring protons in 1-alkyl histidines (N$\tau$) lies in the range 1.1-1.5 Hz, whereas that for the 3-alkyl isomers (N$\pi$) lies in the range 0.9-1.0 Hz. Subsequent crystal structures of histidine analogues have complemented these assignments. The cross-ring coupling constant in molecule 6 was 1.44 Hz. This clearly shows that 6 is the 1-benzyl isomer, as drawn in Reaction Scheme I.

Methylation of (S)-3-ethyl-4-(1,'-benzyl-4'-imidazolyl)methyl-2-oxazolidinone 6 with methyl iodide in acetone gave the imidazolium salt 7 as a crystalline precipitate. Debenzylation of this quaternary derivative 7 to the particularly preferred embodiment, (S)-3-ethyl-5-(1,'-methyl-4,'-imidazolyl) methy-2-oxazolidinone 8, was achieved with ammonium formate and palladium on charcoal in methanol. A large excess of ammonium formate was needed to make the reaction go to completion. Sodium in liquid ammonia decomposed the imidazolium ion 7, but the same conditions debenzylated compound 6 to the NH analogue 9 in good yield. Methylation of 9 with methyl iodide and potassium hydride then gave a 2/1 mixture of N$\tau$-methyl isomer 10 and N$\pi$-methyl isomer 8. Separation by preparative TLC gave each pure target compound, and they were crystallized as fumarate salts.

$^1H$ NMR studies of the 1,5 and 1,4 methyl isomers 8 and 10, respectively, showed that the two isomers have significantly different chemical shifts for the N-methyl and the imidazole protons. This fact can be used to identify and assign regiochemistry to each isomer. As a further test of the regiochemistry of isomers 8 and 10, cross-ring couplings constants for both were measured at 500 MHz. The 1,5-isomer 8 had a cross-ring coupling constant of 1.03 Hz while the 1,4-isomer 10 had a coupling constant of 1.50 Hz.

The guinea pig ileum was used as a primary screening model for studies of the affinities of the compounds at muscarinic receptors, as suggested by *Pharmacological Experiments on Isolated Preparations* (Edinburgh Staff, 2nd Ed., E&S Livingston, 1974). In this in vitro biological system, that is particularly rich in cholinergic muscarinic receptors, N$\pi$-methyl isomer 8 was equipotent with pilocarpine ($ED_{50}=1$ $\mu M$). The N$\pi$-methyl isomer 10 and the NH parent 9 were both weaker muscarinic agonists ($ED_{50}=14$ $\mu M$ and 180 $\mu M$, respectively), whereas the imidazolium salt N$\tau$-benzyl-N$\pi$-methyl derivative 7 and the N$\tau$-benzyl analogue 6 were inactive.

In sum, the biological data from the guinea pig ileum tests show the N$\pi$-methyl isomer 8 is a muscarinic agonist equipotent with pilocarpine. Both the N$\tau$-methyl isomer 10 and NH compound 9 are, like the corresponding N$\pi$-methyl isomer of pilocarpine (neopilocarpine) and N-demethylpilocarpine (pilocarpidine), less active. This indicates that the carbamate nitrogen does not interact with the imidazole pharmacophoric group. Pilocarpine and N$\pi$-methyl isomer 8 have parallel log concentration-response curves, suggesting that they probably activate the same receptor population.

Individual stereoisomers can be separated from mixtures of the two forms by formation and resolution of diastereomeric derivatives followed by resolution, chromatography on stereospecific columns, or other techniques known to the art. The present invention contemplates the individual stereoisomers of derivatives of Formula II, as well as mixtures thereof.

Compounds of the present invention form pharmaceutically acceptable salts with organic and inorganic acids. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzenesulfonic, methane- and ethanesulfonic, hydroxymethane- and hydroxyethanesulfonic, aspartic, and the like.

The salts are prepared by contacting the free base form of the compounds of this invention with a sufficient amount of the desired acid to produce the salt in the conventional manner. The free base forms may be regenerated, if desired, by treating the salt form with a base. For example, dilute aqueous solutions of such bases as sodium hydroxide, potassium carbonate, ammonia, and sodium bicarbonate may be utilized for this purpose.

In the compounds of the present invention pharmaceutically acceptable salts may be formed with suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkyamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine: N-benzylphenethylamine: tris(hydroxymethyl)aminomethane: and the like. (See for example, "Pharmaceutical Salts," J. Pharm. Sci. 66 (1): 1-19 (1977).

The salts are prepared by contacting the free acid form of the compounds of this invention with a sufficient amount of the desired base to produce the salt in the conventional manner. The free acid forms may be regenerated, if desired, by treating the salt form with an acid. For example, a dilute aqueous solution of hydrochloric acid may be utilized for this purpose.

The free acid or base forms of the compounds of this invention differ somewhat from their respective salt forms in such physical properties as melting point and solubility in polar solvents, but the salts are otherwise equivalent to their respective acid or base forms for the purposes of the invention.

EXPERIMENTAL

Melting points were determined in capillary tubes and are uncorrected. $^1$H NMR were recorded at 200 MHz or 250 MHz in either CDCl$_3$ or D$_2$O with Me$_4$Si or 3-(trimethylsilyl)propanesulfonate, respectively, as internal standards. Column chromatography (CC) was performed on 230–400 mesh SiO$_2$ (Merck). Preparative thin-layer chromatography (TLC) was done on pre-coated silica gel GF (20x20 cm, 1000 microns) glass plates (Analtech). Elemental analyses were performed by the Analytical Laboratory, College of Chemistry, University of California, Berkeley, and were within ±0.4% of the calculated values. Tetrahydrofuran (THF) was distilled from sodium/benzophenone and methylene chloride (CH$_2$Cl$_2$) was distilled from P$_2$O$_5$ immediately prior to use.

1-Benzyl-L-Histidine 1. The product 1 was synthesized by treating a solution of L-histidine (80 g, 138 mmol) in liquid ammonia (600 mL) at −70° C. with sodium (36 g) and benzylchloride (48 mL, 416 mmol). The desired product crystallized from a water solution at pH 8 and, after recrystallization from ethanol/water, 7/3, was obtained in a 56% (52.2 g) yield: mp 234–238° C. (lit. mp 248–249° C. corr).

1-Benzyl-L-Histidine Benzyl Ester 2 Di-p-toluenesulfonate. The compound was synthesized as described by du Vigneaud et al. A mixture of 1 (12.20 g, 49.8 mmol), p-toluenesulfonic acid monohydrate (20.84 g, 109.6 mmol), and benzyl alcohol (50 mL, 483 mmol) in carbon tetrachloride (100 mL) was heated under reflux, and the liberated water removed azeotropically. When water no longer distilled off, the reaction mixture was cooled to room temperature and ether was added to the precipitation. Recrystallization from isopropanol gave 2 as the di-p-toluenesulfonate salt in 83% yield (13.94 g): mp 168–170° C. (lit. mp 176–177° C.).

N-Acetyl-1-Benzyl-L-Histidine Benzyl Ester 3. A solution of 2 (23.70 g, 29.6 mmol) in saturated sodium bicarbonate (100 mL), adjusted to pH 8, with sodium carbonate, was extracted with chloroform/isopropanol (4:1, 3×200 mL). The combined organic phase was dried (MgSO$_4$), filtered and evaporated. The residue was refluxed in a mixture of glacial acetic acid (150 mL) and acetic anhydride (5.64 mL, 60 mmol) for 45 min. The reaction mixture was evaporated. The residue was dissolved in water (100 mL) and evaporated until a white solid was obtained. The residue was dissolved in chloroform (300 mL) and washed with a saturated sodium bicarbonate solution (50 mL). The dried (MgSO$_4$) and filtered organic phase was evaporated to give the desired product as a white solid (10.17 g, 96%). Recrystallization from toluene-petroleum ether gave white crystals in a yield of 86%, 9.71 g: mp 113–114° C.; $^1$H NMR (CDCl$_3$) δ7.4 (m, 10 H), 7.15 (s, 1 H), 6.35 (s, 1 H), 5.10 (dd, 2 H), 4.90 (s, 2 H), 4.80 (m, 1 H), 3.00 (m, 2 H), 2.00 (s, 3 H), [α]$^{22}$ −55.3° (c 1.5, chloroform). Anal. (C$_{22}$H$_{23}$N$_3$O$_3$) C, H, N.

1-Benzyl-4-(2′-Ethylamino-3′-Hydroxypropyl) imidazole 4. To a solution of 3 (9.70 g, 25.7 mmol) in THF (200 mL) was added a solution of LiAlH$_4$ (25 mL, 62.5 mmol) in THF. After 16 h at reflux, the reaction mixture was cooled and water (20 mL) was added slowly. The mixture was stirred for 15 min at room temperature and filtered through celite. Sodium chloride was added to separate the aqueous phase, which was extracted with THF (3×200 mL). The combined organic phases were dried (Na$_2$SO$_4$), filtered and evaporated giving a brown oil (7.15 g, 107%). Crystallization of the residue from acetonitrile and ether gave 4 (2.84 g, 43%) as yellow crystals mp 109–110° C.; $^1$H NMR (CDCl$_3$) δ7.45 (s, 1 H), 7.4–7.1 (m, 5 H), 6.68 (s, 1 H), 5.05 (s, 2 h), 3.7–3.4 (m, 2 H), 2.95 (m, 1 H), 2.8–2.6 (m, 4 H), 1.06 (t, 3 H); [α]$^{22}$ 10.2° (c 1.5, methanol). Anal. (C$_{15}$H$_{21}$N$_3$O) C, H, N.

1-Benzyl-4-(2,′(N-benzyloxycarbonyl,N-ethyl) amino-3,′-hydroxypropyl)imidazole 5. Benzyl chloroformate (5.0 mL, 35 mmol) was added drop wise to an ice cooled solution of crude 4 (6.5 g, 25 mmol) in dioxane (70 mL) and aq. LiOH (20 mL, 0.5 N). During the addition of benzyl chloroformate, LiOH (0.5 N) was added incrementally to keep the reaction mixture at pH 8. The reaction mixture was stirred at room temperature for 45 min and evaporated. The residue was dissolved in water (50 mL) and extracted with chloroform (3×200 mL). The combined organic phases were dried (MgSO$_4$), filtered and evaporated. The residue was purified by column chromatography using ethyl acetate as eluent to give 5 (3.13 g, 32%) as a yellow oil: $^1$H NMR (CDCl$_3$) δ7.4 (m, 10 H), 7.1 (s, 1 H), 6.62 (s, 1 H), 5.2–4.9 (m, 4 H), 4.55 (m, 1 H), 4.4–4.0 (m, 2 H), 3.3–3.0 (m, 2 H), 3.0–2.8 (m, 2 H), 0.95 (t, 3 H).

(S)-3-Ethyl-4-(1,′-benzyl-4′-imidazolyl)methyl-2-oxazolidinone 6.

Method A. To a suspension of potassium hydride (9.2 mmol) in THF (10 mL) was added a solution of 5 (3.12 g, 7.96 mmol) in THF (30 mL). The reaction mixture was stirred at room temperature for 1 h. Water (5 mL) was added followed by sodium chloride to separate the phases. The water phase was extracted with THF (3×60 mL) and the combined organic phases were dried (MgSO$_4$), filtered and evaporated. Column chromatography of the residue using ethyl acetate/methanol (9:1) as eluent gave the desired product as an oil (1.3 g, 59%): $^1$H NMR (CDCl$_3$) δ7.55 (s, 1 H), 7.5–7.3 (m, 5 H), 6.78 (s, 1 H), 5.16 (s, 2 H), 4.4–4.1 (m, 3 H), 3.7–3.5 (m, 1 H), 3.3–3.0 (m, 2 H), 2.8–2.6 (m, 1 H), 1.20 (t, 3 H).

Method B. To a solution of phosgene in toluene (7.85 mL, 10.4 mmol) and triethylamine (3.76 mL, 27 mmol) was added a solution of 4 (2.60 g, 10.04 mmol) in methylene chloride (50 mL) at −60° C. The reaction mixture was stirred at −60° C. for 2 h and allowed to warm to room temperature. Water (20 mL) and potassium carbonate were added to pH 9. The water was extracted with methylene chloride (3×100 mL), and the combined methylene chloride phases were dried (MgSO$_4$) and evaporated. The residue was purified by column chromatography to give 6 (1.29 g, 45%). Anal. (C$_{16}$H$_{19}$N$_3$O$_2$H$_2$O) C, H, N.

Imidazolium Iodide 7. A solution of compound 6 (300 mg, 1.1 mmol) and methyl iodide (314 μL, 5 mmol) in acetone (6 mL) was stirred at 60° C. for 48 h. The product 7 crystallized from the solution in a yield of 400 mg (89%): mp 171–179° C.; $^1$H NMR (D$_2$O) δ8.78 (s, 1 H), 7.5–7.3 (m, 5 H), 7.28 (s, 1 H), 5.30 (s, 2 H), 4.5–4.3 (m, 2 H), 4.05 (m, 1 H), 3.80 (s, 3 H), 3.5–3.4 (m, 1 H), 3.3–3.0 (m, 3 H); [α]$^{22}$ 18.7° (c 1.36, 10% methanol). Anal (C$_{17}$H$_{22}$N$_3$O$_2$I) C, H, N.

(S)-3-Ethyl-4-(1′-methyl-5′-imidazolyl)methyl-2-oxazolidinone 8 Fumarate. A suspension of 7 (277 mg, 0.65 mmol), ammonium formate (20 g, 316 mmol) and Pd-C (10%, 130 mg) in methanol (50 mL) was refluxed for 4 h. After cooling to room temperature, the reaction mixture was filtered and evaporated. The residue was dissolved in a saturated sodium bicarbonate solution (30 mL) and the pH adjusted to 8.5 with potassium carbonate. The aqueous solution was extracted with chloroform/isopropanol (2/1, 2×200 mL). The organic phases were washed with sodium thiosulfate (10%, 30 mL), dried (Na$_2$SO$_4$), filtered and evaporated to give the 8 as an oil in 80% yield (110 mg): $^1$H NMR (CDCl$_3$) δ 7.49 (s, 1 H), 6.82 (s, 1 H), 4.4–4.3 (m, 1 H), 4.2–3.9 (m, 2 H), 3.62 (s, 3 H), 3.7–3.5 (m, 1 H), 3.1–2.9 (m, 2 H), 2.78 (m, 1 H), 1.20 (t, 3 H).

The free base 8 was crystallized as the hemifumarate salt by adding a solution of fumaric acid (55 mg, 0.48 mmol) to a solution of 8 (100 mg, 0.48 mmol) in isopropanol. The salt crystallized upon addition of ether: yield, 109 mg, 70%; mp 129–131° C.; $^1$H NMR (D$_2$O) δ 8.70 (s, 1 H), 7.32 (s, 1 H), 6.60 (s, 2 H), 4.6–4.3 (m, 2 H), 1 H), 6.72 (s, 1 H), 4.4–4.1 (m, 3 H), 3.67 (s, 3 H), 3.71–3.5 (m, 1 H), 3.3–3.1 (m, 1 H), 3.00 (dd, 1 H0, 2.70 (dd, 1 H), 1.20 (t, 3 H). The $^1$H NMR spectra of compound 8 was identical with the product from debenzylation of compound 7.

Crystallization of 10 as the fumarate salt from isopropanol gave either the fumarate salt, mp 100–104° C.; Anal (C$_{14}$H$_{19}$N$_3$O$_6$); or the hemifumarate salt, mp 133–135° C.; $[α]_D^{22}$38.3° (c 0.75, H$_2$O); $^1$H NMR (D$_2$O) δ 8.59 (s, 1 H), 7.31 (s, 1 H), 6.53 (s, 1 H), 4.5–4.3 (m, 2 H), 4.15 (m, 1 H), 3.86 (s, 3 H), 3.6–3.4 (m, 1 H), 3.3–3.1 (m, 3 H), 1.20 (t, 3 H). Anal. (C$_{12}$H$_{17}$N$_3$O$_4$) C, H, N.

Table I summarizes the analyses for compounds 3 through 10.

TABLE I

| Compound | Composition | Calculated | | | Found | | |
|---|---|---|---|---|---|---|---|
| | | C | H | N | C | H | N |
| 3 | C$_{22}$H$_{23}$N$_3$O$_3$ | 70.01 | 6.14 | 11.13 | 69.85 | 6.07 | 11.06 |
| 4 | C$_{15}$H$_{21}$N$_3$O | 69.46 | 8.16 | 16.21 | 69.84 | 8.14 | 16.16 |
| 6 | C$_{16}$H$_{19}$N$_3$O$_2$·H$_2$O | 63.35 | 6.98 | 13.85 | 63.14 | 6.95 | 13.45 |
| 7 | C$_{17}$H$_{22}$N$_3$O$_2$I | 47.79 | 5.19 | 9.83 | 47.39 | 5.06 | 9.44 |
| 8. fumarate | C$_{10}$H$_{15}$N$_3$O$_2$·C$_4$H$_4$O$_4$ | 51.69 | 5.89 | 12.92 | 51.28 | 5.89 | 12.74 |
| 9 | C$_9$H$_{13}$N$_3$O$_2$ | 55.37 | 6.71 | 21.53 | 54.96 | 6.64 | 21.35 |
| 9. fumarate | C$_9$H$_{13}$N$_3$O$_2$·C$_4$H$_4$O$_4$ | 50.16 | 5.50 | 13.50 | 49.77 | 5.59 | 12.98 |
| 10. fumarate | C$_{10}$H$_{15}$N$_3$O$_2$·C$_4$H$_4$O$_4$ | 51.69 | 5.89 | 12.92 | 51.65 | 6.01 | 13.11 |
| 10. hemifumarate | C$_{10}$H$_{15}$N$_3$O$_2$·½C$_4$H$_4$O$_4$ | 53.92 | 6.41 | 15.72 | 53.76 | 6.32 | 15.55 |

4.18 (m, 1 H), 3.86 (s, 3 H), 3.6–3.4 (m, 1 H), 3.3–3.1 (m, 3 H), 1.20 (t, 3 H); $[α]^{22}$ 40.3° (c 1.0, H$_2$O). Anal. (C$_{14}$H$_{19}$N$_3$O$_6$) C, H, N.

(S)-3-Ethyl-4-(4'-imidazolyl)methyl-2-oxazolidinone 9 Fumarate. Compound 6 (1.00 g, 3.50 mmol) was dissolved in liquid ammonia (50 mL) at −70° C. and sodium pieces were added to a permanent blue color. The reaction mixture was stirred at −70° C. for 2 min., and ammonuum chloride was added to quench excess sodium. The ammonia was allowed to evaporate spontaneously at room temperature. The residue was dissolved in water (20 mL) and extracted with chloroform/isopropanol (2/1, 2×70 mL). The organic phase was dried (MgSO$_4$), filtered and evaporated. Crystallization from toluene gave 9 (483 mg, 71% yield) as yellow crystals: mp 92–93° C.; $^1$H NMR (CDCl$_3$) δ7.60 (s, 1 H), 6.90 (s, 1 H), 4.4–4.1 (m, 3 H), 3.7–3.5 (m, 1 H), 3.3–3.0 (m, 2 H), 2.9–2.7 (m, 1 H), 1.20 (t, 3 H). Anal. (C$_9$H$_{13}$N$_3$O$_2$) C, H, N.

A sample of 9 (70 mg, 0.36 mmol) was crystallized as the fumarate salt by adding a solution of fumaric acid (42 mg, 0.36 mmol) in isopropanol to a solution of 9 in isopropanol. The 9 fumarate crystallized upon addition of ether (78 mg, 70% yield): mp 157–160° C.; $^1$H NMR (D$_2$O) δ 8.65 (s, 1 H), 7.34 (s, 1 H), 6.68 (s, 2 H), 4.4–4.2 (m, 2 H), 4.18 (m, 1 H), 3.5–3.4 (m, 1 H), 3.3–3.1 (m, 3 H), 1.20 (t, 3 H); $[α]^{22}$ 23.3° (c 0.46, H$_2$O). Anal. (C$_{13}$H$_{17}$N$_3$O$_6$) C, H, N.

(S)-3-Ethyl-4-(1'-methyl-4'-imidazolyl)methyl-2-oxazolidinone 10 Fumarate and (S)-3-Ethyl-4-(1'-methyl-5'-imidazolyl)methyl-2-oxazolidinone 8 Fumarate. A solution of 9 (382 mg, 196 mmol) in THF (40 mL) was added to a suspension of potassium hydride (2.1 mmol) in THF (10 mL). The suspension was stirred for 15 min at room temperature and methyl iodide (141 μL, 2.1 mmol) was added. The reaction mixture was stirred at room temperature for 16 hours, filtered and evaporated. The residue (365 mg, 98%) contained 8 and 10 in a ½ mixture. Separation by preparative TLC gave pure 10 (145 mg, 35% yield) as the upper spot and pure 8 (60 mg, 15% yield) as the lower spot; both compounds were obtained as oils. $^1$H NMR of 10 (CDCL$_3$) δ 7.39 (s, Cross-ring Coupling Constants. The cross-ring coupling constants of compounds 6, 8 and 10 were measured on a Bruker AM500 spectrometer operating at 500.13 MHz. The experiments were done in CDCl$_3$ at room temperature, using the imidazole 2-H resonance. We employed the resolution enhancement techniques of single zero filling and a squared sine bell apodization in addition to homonuclear decoupling of the N-methylene group of 6 or the N-methyl group of 8 and 10.

Guinea Pig Ileum Bioassay. Briefly, a distal portion of guinea pig ileum was cut and a segment (1–1.5 cm) was tied at both ends. One end was connected to a force displacement transducer and the other end to the muscle holder in a 5 ml organ bath. The tissue was suspended with 1 gm tension in Tyrode solution (composition as follows in mM: NaCl 137, KCl 2.7, CaCl$_2$ 1.8, MgCl$_2$ 1.0, NaHCO$_3$ 11.9, Na$_2$HPO$_4$ 0.4, glucose 5.6; pH 7.4) which was aerated with 95% O$_2$ and 5% CO$_2$ and maintained as 37° C. After the tissue was allowed to equilibrate for 45–60 minutes, single doses of agonists were administered into the bath and isotonic contractions were recorded on a Grass polygraph. As may be seen from the data of FIG. 1, the inventive analogues 9, 10, and 8 were cholinergic muscarinic agonists with an increasing order of potency. The particularly preferred analogue 8 was equipotent with pilocarpine.

Although the present invention has been described with reference to specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

We claim:

1. A biologically active compound having the structure

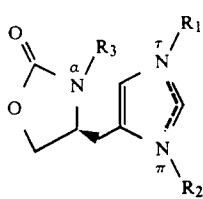

wherein $R_1$ or $R_2$ has less than about 12 carbon atoms and is a primary or secondary alkyl, a primary or secondary aralkyl or a cycloaklkyl and $R_3$ has from at least two carbon atoms to about 8 carbon atoms and is an alkyl, an alkenyl, an alkynyl or a cycloalkyl.

2. A compound having the structure

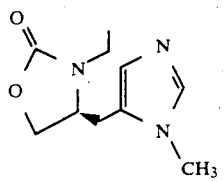

3. A compound having the structure

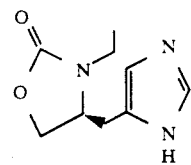

4. A compound having the structure

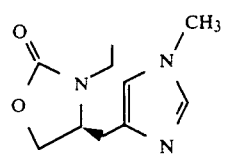

5. An analogue of pilocarpine wherein the lactone ring of pilocarpine has been replaced with a 2-oxazolidinone moiety.

6. The analogue as in claim 5 having a determinable duration of biological activity in the form of muscarinic effects that is increased with respect to pilocarpine.

* * * * *

UNITED STATES PATENT AND TRADEMARK OFFICE
CERTIFICATE OF CORRECTION

PATENT NO. : 5,025,027
DATED : JUNE 18, 1991
INVENTOR(S) : HENRY RAPOPORT AND PER SAUERBERG

It is certified that error appears in the above-identified patent and that said Letters Patent is hereby corrected as shown below:

Column 11, line 13, in Claim 1:  replace "cycloaklkyl" with --cycloalkyl--

Signed and Sealed this

Thirteenth Day of October, 1992

*Attest:*

DOUGLAS B. COMER

*Attesting Officer*   *Acting Commissioner of Patents and Trademarks*